United States Patent [19]
Putnam

[11] Patent Number: 5,334,214
[45] Date of Patent: Aug. 2, 1994

[54] APPARATUS AND METHOD FOR DIVIDING TRANSVERSE CARPAL LIGAMENT

[76] Inventor: Matthew D. Putnam, 5208 Larada La., Minneapolis, Minn. 55436

[21] Appl. No.: 886,778

[22] Filed: May 21, 1992

[51] Int. Cl.$^5$ .............................................. A61B 17/32
[52] U.S. Cl. .................................... 606/170; 128/898
[58] Field of Search ........................ 606/167, 170, 171; 128/3, 4, 6, 7, 898

[56] References Cited

U.S. PATENT DOCUMENTS

| | | | |
|---|---|---|---|
| 762,366 | 6/1904 | Washburn | 606/171 |
| 1,015,472 | 1/1912 | Bredin | 606/171 |
| 3,336,927 | 8/1967 | Klebanoff | 606/167 |
| 5,029,573 | 7/1991 | Chow | 606/170 |

OTHER PUBLICATIONS

Article entitled "Carpal tunnel and ulnar tunnel syndromes and stenosing tenosynovitis", Lee Milford, pp. 459–461.
*Textbook of Hand Surgery*, "Entrapment and Compression Neuropathies", Eversmann, pp. 1433–1437 (1988).
Article entitled "Endoscopic Release of the Carpal Ligament", James C. Y. Chow, M.D. (1990).
Copy of Brochure entitled "Design Features of the Agee Inside Job TM Carpal Ligament Release System", Orthopedic Products Division, 3M Health Care, 3M Center Building, St. Paul, MN 55144-1000 (1989).
Transcription of The American Society for Surgery of the Hand 45th Annual Meeting, Recorded Sep. 23–27, 1990 in Toronto, Canada. Scientific Sessions—No. 1 (1 & 2) "Endoscopic Release of the Carpal Tunnel a Randomized Prospective Multi-Center Study", Dr. John M. Agee, et al.

*Primary Examiner*—Stephen C. Pellegrino
*Assistant Examiner*—William Lewis
*Attorney, Agent, or Firm*—Merchant, Gould, Smith, Edell, Welter & Schmidt

[57] ABSTRACT

As a surgical treatment for carpal tunnel syndrome, guidance mechanism and cutting mechanism are subcutaneously inserted in spaced-apart incisions located by well-known landmarks. The guidance mechanism is placed below the transverse carpal ligament, and the cutting mechanism is placed above it. As the cutting mechanism is advanced, it is guided by the guidance mechanism and the knife portion divides the carpal ligament.

10 Claims, 3 Drawing Sheets

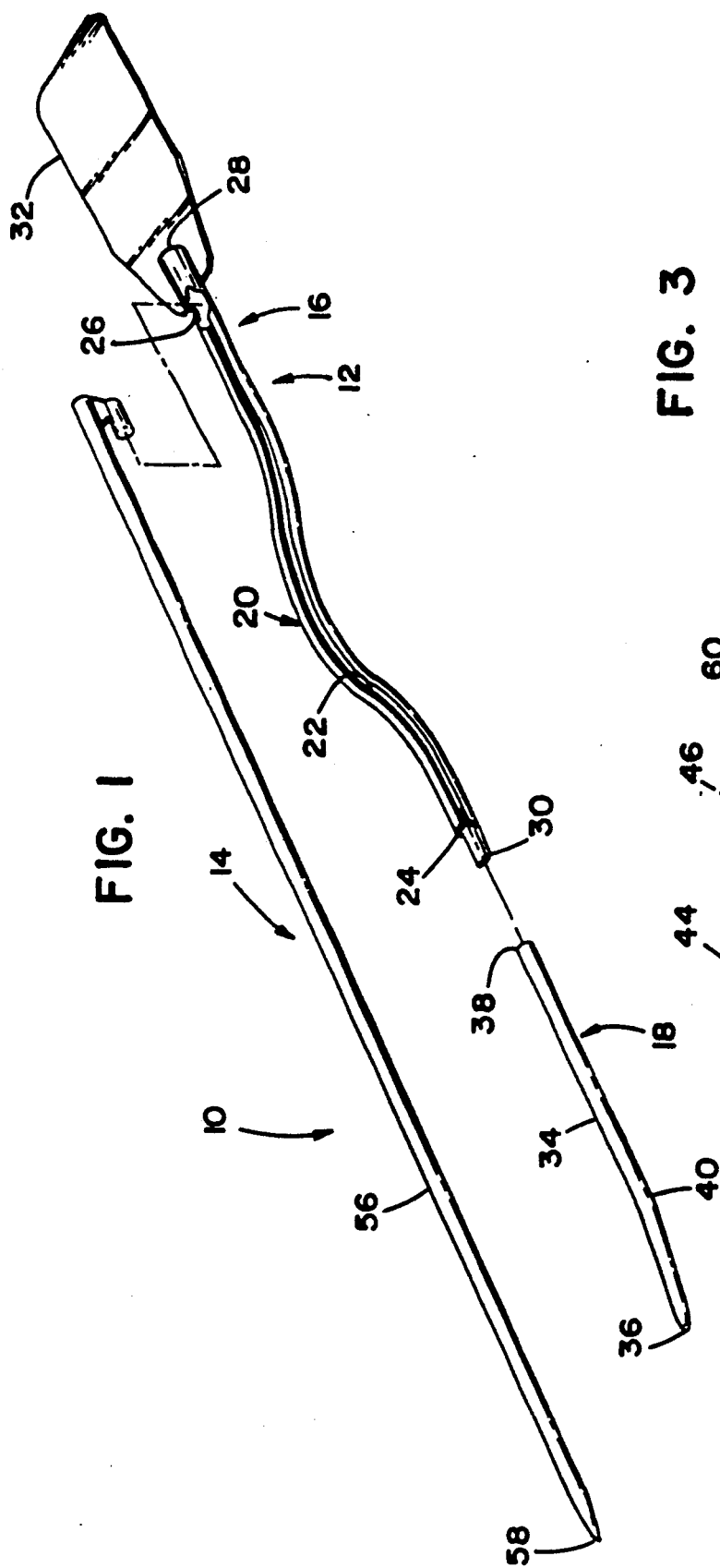
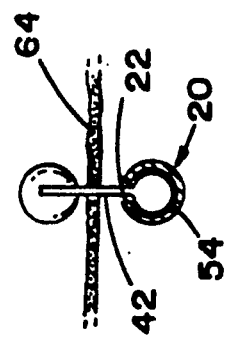
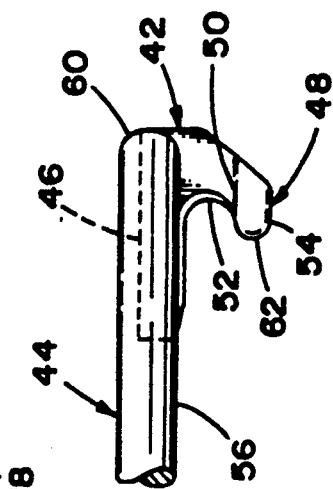

APPARATUS AND METHOD FOR DIVIDING TRANSVERSE CARPAL LIGAMENT

FIELD OF THE INVENTION

The present invention is directed to surgical equipment, particularly, apparatus for severing the transverse carpal ligament in a person's hand in treatment of carpal tunnel syndrome.

BACKGROUND OF THE INVENTION

Carpal tunnel syndrome results from compression of the median nerve within the carpal tunnel of the hand. It occurs most often in people between 30 and 60 years old and is several times more frequent in women than in men. Any condition that crowds or reduces the size of the carpal tunnel may initiate the symptoms. If there are mild symptoms present, injection of hydrocortisone into the carpal tunnel may afford relief. When symptoms are persistent and progressive, however, division of the deep transverse carpal ligament is recommended.

In the 1950's, a procedure was developed for releasing the carpal tunnel ligament by pushing a closed blade. The procedure was rapidly discredited because of its inaccuracy and consequent failure rate. The original blade assembly resembled a meniscatome blade, but because the pathway of the blade was not directly controlled, it was possible for the surgeon to aim incorrectly and thereby sever nerves, arteries, or tendon structures. This was a truly blind procedure without guidance from additional devices or visualization.

Shortly after that, surgeons began using an open surgical technique, which is still the prevalent surgical treatment. Briefly, various curved or zig-zag incisions are made from a point ulnar to and paralleling the thenar crease to approximately the flexor crease of the wrist. The skin and subcutaneous tissue are incised, and the transverse carpal ligament then divided. The incision is closed and the wound drained as needed.

Following open surgical release, swelling at the base of the palm superficial to the carpal tunnel tends to persist for 12 to 16 weeks. During this time, the patient often experiences aching pain in the thenat or hypothenar eminences. Gripping activity aggravates the pain and may cause shooting sensations into the forearm. Resolution of the swelling is usually accompanied by relief of the pain.

Further results from open surgical release often include a tender scar, a hospital stay, and sometimes an incomplete release of the transverse carpal ligament.

A recent surgical procedure involves the use of an endoscope. The concept of the endoscopic technique is to permit constant visualization during the surgery. Briefly, the procedure requires a surgeon and an assistant. Approximate landmarks on the hand establish entry and exit portals which are marked. Incision at the proximal entry portal on the volar surface of the wrist is made using appropriate surgical incision tools. A slotted cannula assembly is guided into the entry portal incision space. The wrist and fingers of the hand must then be bent in full hyperextension. As a consequence, this procedure is not available to patients with stiff wrists which are unable to be hyperextended. An obturator fitted in the cannula advances against the transverse carpal ligament, using it as a ceiling. When the tip of the obturator reaches the pre-marked exit portal, a small incision is made and the slotted cannula assembly is pushed through. The obturator is removed from the cannula. A video endoscope is then inserted into the slotted cannula. The instrument is used to visualize the entire carpal ligament. If difficulty in accessing the ligament is experienced, the video endoscope must be removed, the obturator reinserted, the cannula assembly removed, and the placement procedure started again. When the surgeon is confident of understanding the carpal ligament, the video endoscope is moved out of the way with respect to the slotted cannula and various knife tools are inserted with the knife extending upwardly from the slot. After some cutting is done, the endoscope may be moved into place to view the cut. In this way, eventually the ligament is completely divided. Following removal of the video endoscope, the obturator is reinserted and the assembly removed with the wound then being sutured and given appropriate care.

The endoscopic release procedure seems to result in a less tender scar and possibly a faster recovery, perhaps 2 to 4 weeks. The costs of the procedure, however, are higher. There is a hospital stay. The procedure requires wrist hyperextension which is not possible with some patients. Although the visualization concept is attractive, there is considerable question whether anything useful is really seen.

In a recent study, with patients not receiving worker's compensation, it was verified that endoscopic patients return to work in about one-third the time of those having open surgical release. The endoscopic procedure is presently not recommended, however, since the present procedure does not address the possibility of cutting nerves and vessels over the ligament and with some patients there has been nerve injury.

Thus, open surgical release procedure remains the most prevalent treatment for carpal tunnel syndrome having more advanced symptoms so that division of the transverse carpal ligament is indicated. Some of the more positive results, however, of the endoscopic release technique, such as, less tender scar and faster recovery time, show that improvements are possible. This gives impetus to development of the present invention. The present invention requires appropriate testing, but is expected to provide a more reliable and safer, much quicker and less expensive surgical technique than the endoscopic technique and should result in less pain and tenderness and faster recovery.

SUMMARY OF THE INVENTION

The invention is directed to apparatus for dividing the transverse carpal ligament. The apparatus includes guidance mechanism and cutting mechanism. The guidance mechanism passes under the carpal ligament in such a way that it extends subcutaneously between a pair of incisions in the volar side of the palm. The cutting mechanism passes over the carpal ligament while also extending subcutaneously between the incisions. In this way, the cutting mechanism can be guided by the guidance means between the incisions to accomplish the division.

The invention is also directed to the method for using the apparatus. The method includes the steps of preparing the hand for a surgical procedure. After making first and second incisions in the hand and with the hand flat, the guidance means is passed subcutaneously from the first incision under the transverse carpal ligament to the second incision. Cutting mechanism is then passed subcutaneously from the first incision over the transverse carpal ligament to the second incision. The cutting mechanism has a knife at an end with a guide member which movably connects to the guiding portion of the guidance mechanism. The knife is advanced to cut the transverse carpal ligament. The knife exits the hand at the second incision. The guiding portion is then removed and the incisions are appropriately sutured and given care.

The present apparatus and method is accurate and reproducible. The guidance mechanism is placed below the carpal ligament and the cutting mechanism is placed above it. The tissue in between is cut and cut along the path defined by the guidance mechanism. The procedure is easy and can be performed in the doctor's office, so it is much less costly than known procedures. It is expected that recovery time will be faster than known procedures and pain and tenderness less. Since the wrist can remain flat, as opposed to being hyperextended, the procedure should be available to all patients. Additionally, the procedure as described visualizes the superficial palmar arch as necessary through the distal incision as well as the distal aspect of the transverse carpal ligament, which is important to success of any of the procedures described to date. Visualizing the transverse carpal ligament distally allows for the device to be positioned accurately and the device itself prevents excursion of the knife into Guyoh's canal, which is possible with the upward cutting blades utilized through the endoscopic slotted cannula, which do not control the path of the blade beyond the under surface or volar aspect of the transverse carpal ligament. The endoscopic slotted cannula systems allow for the surgeon to inadvertently pass sharp knife instruments into Guyon's canal, whereas this guided (anatomic guided C.T.R. system) blade cannot pass into Guyoh's canal, as it is guided on both the dorsal and volar aspects of the transverse carpal ligament.

BRIEF DESCRIPTION OF THE DRAWINGS

FIG. 1 is a perspective view of apparatus in accordance with the present invention;

FIG. 2 is a side view of the knife mechanism;

FIG. 3 is a cross-sectional view of the apparatus of FIG. 1, from Just in front of the flat handle looking away from it;

DETAILED DESCRIPTION OF THE PREFERRED EMBODIMENT

Figure 4:
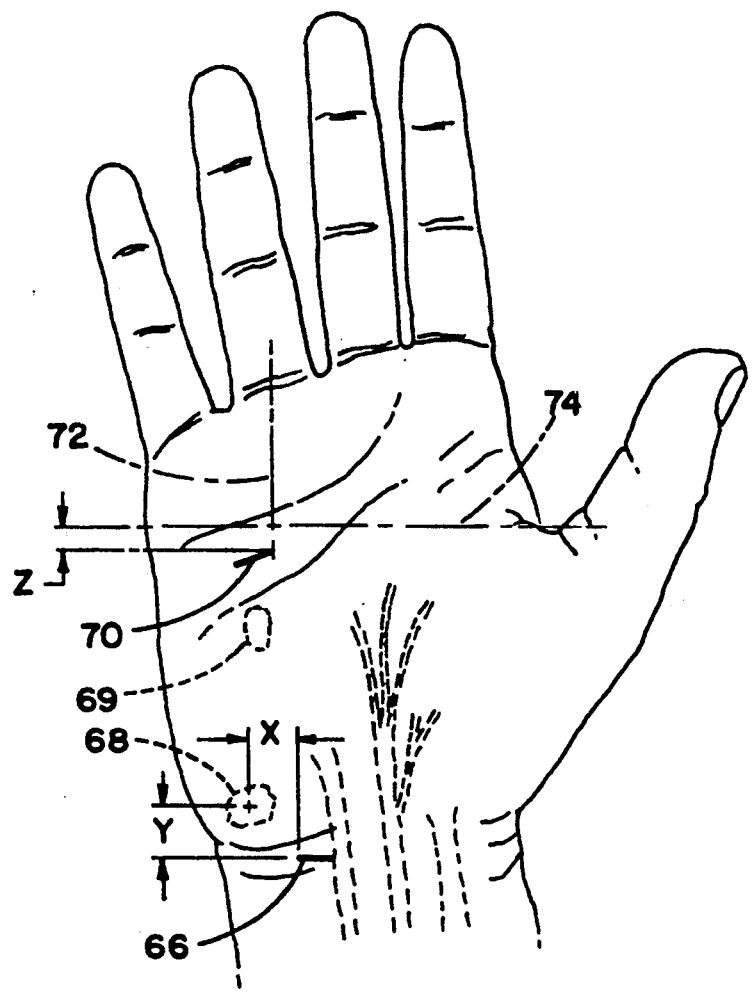
FIG. 4 is a top view of the palm of a hand.

Referring now to the drawings wherein like reference numerals designate identical or corresponding parts throughout the several views, and more particularly to FIGS. 1-3, apparatus in accordance with the present invention is designated generally by the numeral 10. Apparatus 10 includes guidance mechanism 12 and cutting mechanism 14. Guidance mechanism 12 further includes mechanism 16 for guiding cutting mechanism 14 and mechanism 18 for leading the guiding mechanism 16.

Guiding mechanism 16 includes a tube 20 with a slot 22 running from distal end 24 to an entrance opening 26 near the proximal end 28. Tube 20 should have as small a diameter as possible within the constraint that knife 42 must be of a sufficient size to cut the transverse carpal ligament easily. The width of knife 42 then dictates a somewhat larger diameter for guide member 48. The inside diameter of tube 20 is only slightly larger than the diameter of guide member 48. The wall thickness of tube 20 depends on the material used, but in any case, tube 20 must have sufficient structural rigidity to provide a steady guiding channel for guide member 48 to follow from entrance opening 26 to distal end 24. Tube 20 is preferably made from stainless steel, although other materials are appropriate as well.

Tube 20 is formed to include a bimodal curve with the convex side toward the thumb of the particular hand. At distal end 24, portions of each side of tube 20 are cut away to leave a bottom extension 30 extending a short distance beyond the slotted tubular portion of tube 20. Extension 30 protects the patient's hand as cutting mechanism 14 is pulled from tip 20. At the proximal end 28 of tube 20, in a region proximal of entrance opening 26, a flat handle 32 is attached. The planar orientation of handle 32 is approximately parallel with extension 30 so that both elements lie relatively flat on the patient's skin. Handle 32 is attached to tube 20 by weld or other known fastening mechanism.

The leading mechanism 18 is a rod 34 with a narrowed tip 36. Rod 34 is preferably made of a plastic material. The end 38 opposite tip 34 is formed to fit snugly in the distal end 24 of tube 20. Leading mechanism 18 includes a bend 40 so that when mechanism 18 is inserted in tube 20, tip 36 is directed somewhat upwardly. In this way, during insertion of guidance mechanism 12, tip 36 can be used to palpate the under surface of the carpal ligament.

As shown in FIGS. 1 and 2, cutting mechanism 14 includes a knife 42 having a mechanism 44 for pulling at a first end 46 and a mechanism 48 for being guided while being pulled by the pulling mechanism at the second end 50 of knife 42. Knife 42 has a sharpened edge 52 facing the distal end 24 of guiding mechanism 16 when guide member 54 is in tube 20. Edge 52 has a concave arcuate shape. Knife 42 has width to provide sufficient strength to cut the carpal ligament. Slot 22 is only slightly wider than a portion of knife 42 so that knife 42 can be pulled the entire length of slot 22.

Pulling mechanism 46 is an elongated, flexible rod 56 having a narrowed tip 58. The first end 44 of knife 42 is fastened in a slot in proximal end 60 of rod 56. Rod 56 is preferably made from polvinylchloride (PVC) or an equivalent material.

Guide member 54 is a unitary enlargement of blade 42 at second end 50. Guide member 54 is cylindrically shaped with a diameter slightly smaller than the inside diameter of tube 20. The diameter of guide member 54 is somewhat larger than the width of knife 42. The distal tip 62 is preferably semi-hemispherical. Guide member 54 is sufficiently long to prevent excessive wiggling in tube 20 with its length preferably approximately centered on the center of sharpened edge 52. Entrance opening 26 must be sufficiently large to easily receive guide member 54. Extension 30 must be sufficiently long to provide a platform for guide 54 on which to rest when it exits distal end 24 of tube 20 before being lifted and separated from guiding mechanism 16.

In FIG. 3, the relative relationship between tube 20 and guide member 54 is shown, with knife 42 extending through slot 22. Knife 42 is shown relative to carpal ligament 64.

Figure 5:
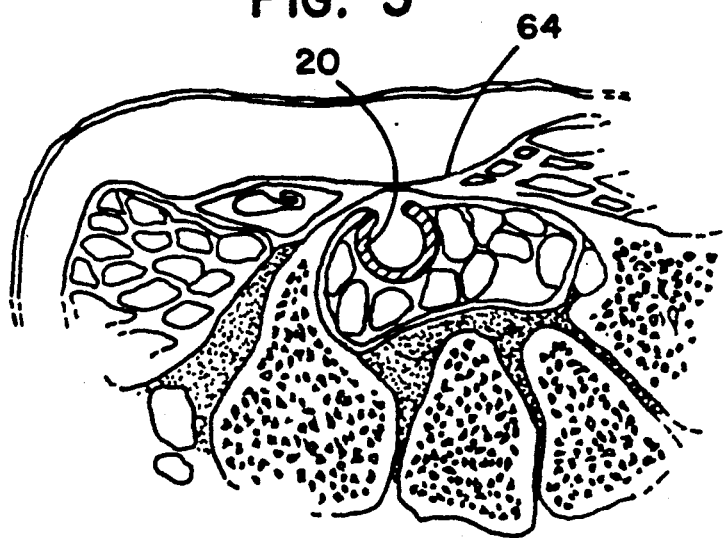
FIG. 5 is a cross-sectional view laterally across the hand in the region of the transverse carpal ligament.
Figure 6:
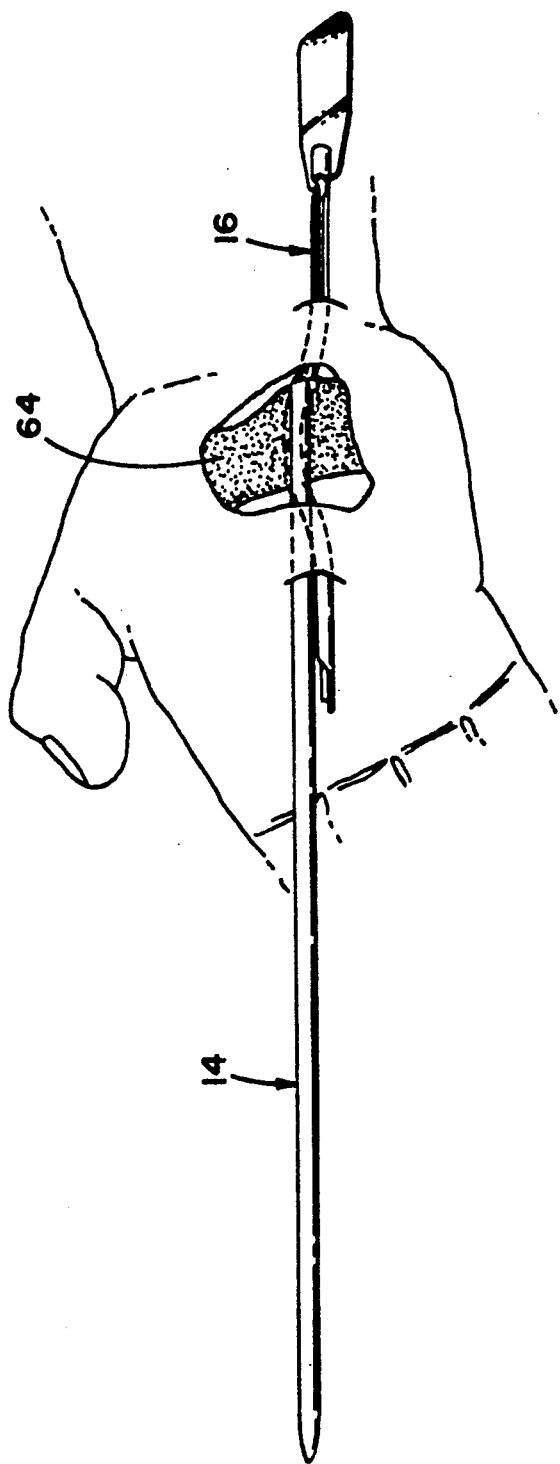
FIG. 6 is a perspective view of the hand and the apparatus of FIG. 1 with a portion of the hand cut away to show the apparatus in position during surgical division of the carpal ligament.

In use, with reference to FIGS. 4-6, apparatus 10 functions in accordance with a relatively simple surgical procedure to divide the transverse carpal ligament. The hand is first prepared for a surgical procedure in a fashion known to those skilled in the art. First and second incisions are required. The first incision 66 is directed radially approximately 1 centimeter in length from a point about 1 centimeter X radial from the center of the pisiform bone 68 and about 1 centimeter Y proximal therefrom. The second incision is a little more than 1 centimeter Z proximal from and parallel to a line 70 bisecting and on the ulnar side of an intersection between the ring line 72 and a line 74 across the palm from the distal border of the thumb.

With the hand flat, the guidance mechanism is subcutaneously passed from the first incision under the transverse carpal ligament to the second incision. As known to those skilled in the art, various nerves and arteries and other anatomic features must be carefully avoided. Tip 36 of leader rod 34 can be used to palpate the underside of the carpal ligament as the guidance mechanism is advanced. This allows a second incision to be placed where the guard is palpated surfacing from below the transverse carpal ligament. The guard is lifted from the incision, verifying its location just distal to the transverse carpal ligament. The patient is asked to move their fingers, verifying that tendons have not been entrapped. The guidance mechanism 12 is advanced so that entrance opening 26 is proximal and outside first incision 66. Distal opening 24 is distal and outside second incision 70. Extension 30 and handle 32 are relatively flat against the skin. Leader rod 34 is removed from tube 20 so that distal end 24 is open. Tube 20 is shown in cross-section relative to carpal ligament 64 and several other anatomic features in FIG. 5. Cutting mechanism 14 is next passed subcutaneously into first incision 66 and over transverse carpal ligament 64 to project out of second incision 70. Again, as known to those skilled in the art, various anatomic features must be carefully avoided. Cutting mechanism 14 is advanced sufficiently far so that guide member 48 can be placed in entrance opening 26. Rod 56 is then gently pulled to advance knife 42 while guide member 48 tracks tube 20. As knife 42 is advanced, transverse carpal ligament 64 is cut. Eventually, knife 42 exits second incision 70, and guide member 48 reaches distal end 24 of guiding mechanism 16 so that cutting mechanism 14 can be separated from guiding mechanism 16. The first and second incisions 66 and 70 are sutured and otherwise given post-operative care as known to those skilled in the art.

The entire procedure is done with local anesthesia and can be done in the doctor's office. Since the guiding means 16 and cutting means 14 are placed accurately before any cutting is done, and since knife 42 then follows an accurate path as established by guiding mechanism 16, the carpal ligament division is accurate and reproducible. It is expected that the present technique will lead to less tenderness and pain and a shorter recovery period. The present technique is clearly less expensive than known procedures. The present apparatus and technique considerably simplifies the surgical solution to carpal tunnel syndrome, and is a significant improvement over known procedures.

Finally, even though numerous characteristics and advantages of the present invention have been set forth in the foregoing, together with details of structure and function, it is understood that the disclosure is illustrative only. Changes made in detail, especially in matters of shape, size, and arrangement of parts and with respect to procedure, are within the principles of the invention to the full extent indicated by the general meaning of the terms in which the appended claims are expressed.

What is claimed is:

1. Apparatus for dividing a transverse carpal ligament in a hand of a person, comprising:
    a knife having means for pulling at a first end and means for being guided while being pulled by said pulling means at a second end;
    means for guiding said guided means, said guiding means having distal and proximal ends; and
    means for leading said guiding means, said leading means being detachable from said distal end of said guiding means;
    wherein said leading means is directed into a first incision in said hand and under said carpal ligament and out a second incision to place said guiding means, said leading means then being detached, and wherein said pulling means is directed into said first incision and over said carpal ligament and out said second incision to allow placement of said guided means in said guiding means, so that said knife can be pulled by said pulling means from said first incision to cut said carpal ligament to said second incision, said guided means thereupon being removed from said guiding means and said guiding means being removed from said hand.

2. Apparatus in accordance with claim 1 wherein said pulling means is an elongated, flexible rod having a narrowed tip.

3. Apparatus in accordance with claim 1 wherein said guiding means includes a bimodal curve with convex side toward the thumb.

4. Apparatus in accordance with claim 1 wherein said guiding means includes a tube with a slot running from said distal end to an entrance opening for said guided means near said proximal end, said slot having a width less that the inside diameter of said tube.

5. Apparatus in accordance with claim 4 wherein said guided means includes a guide member adapted to fit closely within said tube, said guide member having a width perpendicular to said knife which is greater than the width of said slot, said guide member fitting through said entrance opening, said knife having a portion which can be moved through said slot from said entrance opening to said distal end.

6. Apparatus in accordance with claim 5 wherein said knife has a sharpened edge facing said distal end of said guiding means when said guide member is in said tube.

7. Apparatus in accordance with claim 4 wherein said leading means includes a rod with a narrowed tip and with an end opposite adapted to fit snugly in said distal end of said tube, said rod further including a bend which directs said tip upwardly as said rod passes under the carpal ligament.

8. Apparatus for dividing a transverse carpal ligament in a hand of a person, comprising:
    guidance means, extending simultaneously between incisions in the volar distal forearm and the palm, for passing on one side of the carpal ligament; and
    means for dividing said carpal ligament, said dividing means including means for being guided by said guidance means, said dividing means further including a member which allows a person to advance said dividing means passed said carpal ligament, said member being connected to said guided means and extending spaced from said guidance means on an opposite side of said carpal ligament as said one side and through one of said incisions.

9. Apparatus in accordance with claim 8 wherein said dividing means still further includes a knife extending between said guided means and said member.

10. A method for using apparatus including means for dividing a transverse carpal ligament in a hand of a person, said dividing means having a pulling member and a guide member with a knife therebetween, said method comprising the steps of:
preparing said hand for a surgical procedure;
making first and second incisions in said hand;
with the wrist in a neutral position, passing guidance means subcutaneously from said first incision on one side of the transverse carpal ligament to said second incision;
passing said pulling member subcutaneously from said first incision on an opposite side of said transverse carpal ligament as said one side to said second incision, said guide member movably connecting to said guidance means;
pulling said pulling member to advance said guide member along said guidance means to allow said knife to cut said transverse carpal ligament, said diving means exiting the hand at said second incision;
removing said guidance means and
suturing said first and second incisions.

* * * * *